United States Patent [19]

Kalopissis et al.

[11] 3,978,061
[45] Aug. 31, 1976

[54] KERATIN FIBER DYE COMPOUNDS

[75] Inventors: Gregoire Kalopissis, Paris; André Bugaut, Boulogne-sur-Seine; Vahan Zorayan, Enghein-les-Bains, all of France

[73] Assignee: L'Oreal, Paris, France

[22] Filed: Apr. 20, 1973

[21] Appl. No.: 352,995

Related U.S. Application Data

[62] Division of Ser. No. 78,923, Oct. 7, 1970, Pat. No. 3,742,048, which is a division of Ser. No. 728,750, May 13, 1968, Pat. No. 3,617,164.

[30] Foreign Application Priority Data

May 16, 1967 Luxemburg............................ 53676
May 16, 1967 Luxemburg............................ 53677
May 16, 1967 Luxemburg............................ 53678

[52] U.S. Cl.................. 260/570.5 P; 260/247.5 R; 260/293.79; 260/470; 260/471 R; 260/488 CD; 260/518 R; 260/556 AR; 260/556 B; 260/558 A; 260/562 R; 260/573; 260/577; 424/70
[51] Int. Cl.².................. C07C 87/60; C07D 295/12
[58] Field of Search...... 260/247.5, 293.79, 570.5 P

[56] References Cited
UNITED STATES PATENTS 3,646,216 2/1972 Marshall et al............... 260/570.5 P
3,743,678 7/1973 Halasz.......................... 260/570.5 P

OTHER PUBLICATIONS

Hoffman et al., CA, vol. 55:25990(d) (1961).
Jauregg, CA, vol. 58:4581(d) (1963).

*Primary Examiner*—Natalie Trousof
*Attorney, Agent, or Firm*—Cushman, Darby & Cushman

[57] ABSTRACT

A compound of the formula

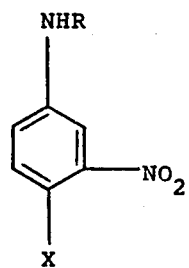

wherein R is -alkylaminodialkyl, -alkylmorpholino or -alkylpiperidino and X is halogen, the alkyl portion of R having 1 to 6 carbon atoms, and the salts of said compound. This compound can be used as an intermediate to produce hair dyes.

2 Claims, No Drawings

KERATIN FIBER DYE COMPOUNDS

This is a division of application Ser. No. 78,923, filed Oct. 7, 1970, now U.S. Pat. No. 3,742,048 which is a division of application Ser. No. 728,750, filed May 13, 1968, now U.S. Pat. No. 3,617,164.

It is an object of the present invention to provide a new chemical compound responding to the formula:

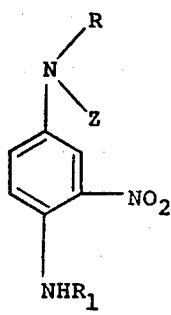

in which R represents a lower alkyl, which may or may not be substituted, and in particular a hydroxyalkyl, carboxyalkyl, carbethoxyalkyl, carbamylalkyl, halogenoalkyl or aminoalkyl radical. The aminoalkyl may, or may not be substituted on the amine function, the nitrogen atom of which may form part of a heterocyclic ring. In the above formula Z may be an

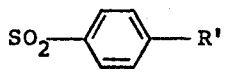

radical, or a

radical, with R' representing a hydrogen atom, a methyl group, or an $NO_2$ group, and R'' representing a hydrogen atom, or a lower alkyl, while $R_1$ represents a lower alkyl, a lower hydroxyalkyl, a lower alkoxyalkyl, or a $-(CH_2)_n$

chain in which $n$ is a whole number between 2 and 6 inclusive, and $R_2$ and $R_3$ which may be identical or different, represent a hydrogen atom, a lower alkyl, or a lower hydroxyalkyl, while the nitrogen atom adjacent $R_2$ and $R_3$ may form therewith a heterocyclic radical such as a morpholino or piperidino radical, the alkyl portions of the radicals R, R'', $R_1$, $R_2$, and $R_3$ having 1–6 carbon atoms.

Another object of the present invention is to provide new quaternary derivatives corresponding to the compounds of formula (I), when these compounds have a quaternizable tertiary amine function.

It should be noted that the compounds of formula (I) are particularly adapted to be used to dye keratinic fibers in general, and especially hair. They have an excellent affinity for keratinic fibers, good stability when exposed to light and inclement weather, and are readily soluble in water.

A further object of the present invention is to provide a composition for dyeing human hair essentially characterized by the fact that it comprises, in solution, at least one dye selected from the group consisting of the compounds responding to formula (I) and their quaternary derivatives.

The dyeing compositions according to the invention are preferably simple aqueous solutions having a pH value lying generally between 4 and 10, and preferably between 7 and 10.

Moreover, the dyeing compositions according to the invention may comprise various ingredients currently used in hair dyeing compositions, such for example as organic solvents, thickening agents, detergents, emollients, perfumes and lacquers. The dyes according to the invention may also be mixed with each other and with other dyes such as nitro dyes, azo dyes, anthraquinone dyes, or any other type of dye conventionally used to dye hair.

The application of these dyeing compositions to the hair does not necessitate the addition of an oxidizing agent. The time of contact with the hair may vary within broad limits, but falls preferably between 5 and 30 minutes. The temperature at which said compositions are applied may also be varied, but they are preferably used at room temperature. The concentration of the dye may be varied within broad limits, but lies preferably between 0.1% and 3% by weight.

It is a further object of the present invention to provide a method of dyeing hair essentially characterized by the fact that a dyeing composition as hereinbefore defined is applied to the hair for between 5 and 30 minutes, and the hair is then washed, rinsed, and dried.

The present invention also comprises a method of preparing the compounds of formula (I) essentially characterized by the fact that, in the first step parahalogenometanitranilines or arylsulfonamides responding to the formula:

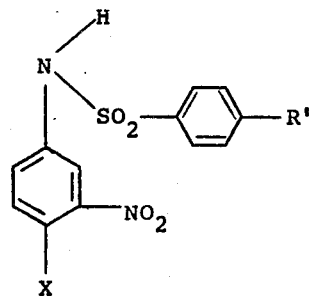

in which R' has the significance hereinbefore indicated, and X represents a halogen atom (preferably chlorine) are alkylized. This step is followed in the case of the arylsulfonamides of formula II, by acid hydrolysis, so as to obtain a compound responding to the formula:

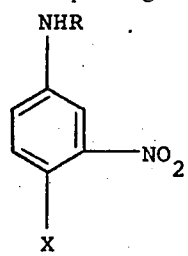

(III)

in which X and R have the significances hereinbefore indicated. Then, in a second step, the compound according to formula III is amidified to transform it into a derivative responding to the formula:

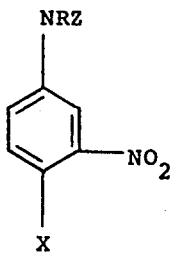

in which X and R have the significances hereinbefore indicated and Z represents either an

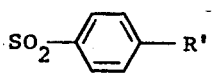

radical, in which R' has the significances hereinbefore indicated, or a

radical in which R'' has the significance hereinbefore indicated. This is followed by a third step in which the compound of formula IV is reacted with an amine having the formula $R_1NH_2$, in which $R_1$ has the significance hereinbefore indicated.

The compounds responding to formula (I) may be quaternized in a conventional manner, using a quaternizing agent such as methyl sulfate or an alkyl or aryl halide.

It is also an object of the present invention to provide the intermediates obtained in the course of the above described process, per se. In particular, it is desired to obtain chemical compounds responding to the formula:

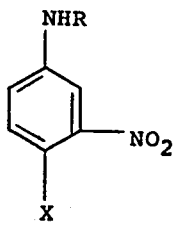

and their salts (particularly their hydrohalides) as well as the chemical compounds responding to the formula:

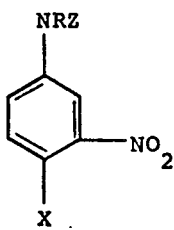

and their salts (particularly their hydrohalides). In these formulae R, X and Z have the significances hereinbefore indicated.

The present invention also encompasses the methods of making the new intermediates responding to formulas (III) and (IV). These processes consist of the first and second steps of the method of making the compound of formula (I), as hereinbefore described.

In order that the invention may be better understood, several examples of methods of making the intermediates of formulas (III) and (IV) and the final compound of formula (I), as well as several dyeing compositions made with the compounds of formula (I) will now be described.

In the first series of examples, the preparation of several compounds responding to formula (III) will be described.

EXAMPLE 1

Preparation of 2-nitro-4-N-β-hydroxyethylamino chlorobenzene by direct alkylation A mixture containing 0.070 mol (12 g) of 2-nitro-4-amino chlorobenzene is heated in a boiling water bath with 0.14 mol (25 g) of 70% glycol bromohydrin, 10 cc of water and 7 g of calcium carbonate. After heating for two hours, 0.14 mol of 70% glycol bromohydrin and 7 g calcium carbonate are added and the heating continued for another 2 hours. After cooling, 150 cc of normal hydrochloric acid are poured in, and the mixture filtered. After alkalizing with ammonia, drying yields 13.5 g of a product which contains a little 2-nitro-4-N-β-hydroxyethylamino chlorobenzene. After recrystallization in a mixture of water and ethanol, 2-nitro-4-N-β-hydroxyethylamino chlorobenzene is obtained. This melts at 72°C and is the same as the product hereinafter described in Example 4.

EXAMPLE 2

Preparation of 2-nitro-4-(N-β-diethylaminoethyl)amine chlorobenzene by direct alkylation.

This product is prepared by adding diethylaminoethylchloride hydrobromide to a solution of 2-nitro-4-amino chlorobenzene in the presence of calcium carbonate in water and alcohol which has first been brought to reflux. After keeping this at reflux for nine hours, it is boiled dry. The filtrate is cooled, and the desired product is isolated in the form of its monohydrobromide. The corresponding base prepared from this monohydrobromide is an oil, which is dissolved hot in a 1/10 normal solution of hydrochloric acid. After cooling, drying yields the monohydrochloride of 2-nitro-4-N-(β-diethylaminoethyl)-4-amino chlorobenzene which after recrystallization in 1/10 normal hydrochloric acid, melts and decomposes at 191°C, and is the same as the product hereinafter described in Example 5.

EXAMPLE 3

Preparation of N-methyl-para chlorometanitraniline by alkylation with arylsulfonamides.

First step, alkylation.

0.4 mol (125 g) of 2-nitro-4-benzenesulfonylamino chlorobenzene is dissolved in 600 cc of a normal sodium hydroxide solution at 30°C. 1.6 mols (125 cc) of methyl sulfate are added little by little, while keeping the temperature between 35° and 40°C and the pH value near 9 by successive additions of a normal sodium hydroxide solution. The reaction mixture is then left to stand for 6 hours at room temperature. Cooling, drying and washing then yields 138 g of crude 2-nitro-4-N-methyl-N-benzene sulfonylamino benzene which, after recrystallization in ethyl acetate, melts at 119°C. Analysis of this product shows the following results:

| Analysis | Calculated for $C_{13}H_{11}N_2ClSO_4$ | Found |
|---|---|---|
| C % | 47.78 | 47.86–47.89 |
| H % | 3.37 | 3.43– 3.52 |
| N % | 8.57 | 8.27– 8.46 |

Second step: Hydrolysis 0.168 mol (55.2g) of 2-nitro-4-(N-methyl,N-benzylsulfonyl)amino chlorobenzene is added little by little, to 275 cc of sulfuric acid at 0°C. When it is completely dissolved, the reaction mixture is left standing for 12 hours at room temperature, and then poured into 2 liters of ice water, after which it is alkalized with a 5 times normal solution of sodium hydroxide. Drying and washing with water yields 38.5 g of 2-nitro-4-N-methylamino chlorobenzene, which melts at 56°C. Analysis of the product yields the following results:

| Analysis | Calculated for $C_7H_7N_2O_2Cl$ | Found |
|---|---|---|
| C % | 45.08 | 44.87–44.96 |
| H % | 3.72 | 3.84– 3.87 |
| N % | 15.01 | 15.15–15.25 |

EXAMPLE 4

Preparation of N-β-hydroxyethyl-parachlorometanitraniline by alkylation of an arylsulfonamide.

First step: Alkylation 0.097 mol (30 g) of 2-nitro-4-N-benzene-sulfonylamino chlorobenzene is dissolved in 195 cc of a one-half normal sodium hydroxide solution which has first been brought to 60°C. While maintaining the reaction mixture at this temperature, 0.5 mol (33.3 cc) of glycol chlorohydrin is added drop by drop while stirring vigorously. A 5 times normal sodium hydroxide solution is added simultaneously to keep the pH between 10.5 and 11. The mixture is maintained at 60°C for about five hours and then left standing for 12 hours at room temperature. Drying and washing with water yields 34 g of 2-nitro-4-(N-β-hydroxyethyl-N-benzenesulfonyl)-amino chlorobenzene which, after recrystallization in methanol, melts at 119°C. Analysis of the product yields the following results:

| Analysis | Calculated for $C_{14}H_{13}N_2O_5S\ Cl$ | Found |
|---|---|---|
| N % | 7.85 | 7.82–7.84 |
| S % | 8.97 | 8.96–9.14 |

Second step: Hydrolysis 0.0056 mol (2 g) of 2-nitro-4-(N-β-hydroxyethyl-N-benzenesulfonyl)-amino chlorobenzene is heated for an hour and a half in a boiling water bath in 25 cc of concentrated hydrochloric acid. After cooling and dilution, this is alkalized with ammonia and drying yields 0.9 g of N-β-hydroxyethyl-parachlorometanitraniline which, after recrystallization in benzene, melts at 72°C. Analysis of the product yields the following results:

| Analysis | Calculated for $C_8H_9N_2O_3Cl$ | Found |
|---|---|---|
| C % | 44.34 | 44.61–44.61 |
| H % | 4.15 | 4.08– 4.23 |
| N % | 12.93 | 13.04–12.98 |

EXAMPLE 5

Preparation of 2-nitro-4-(N-β-diethylaminoethyl)amino chlorobenzene monohydrochloride by alkylation of an aryl sulfonamide.

First step: alkylation.

0.1 mol (31.25 g) of 2-nitro-4-N-benzenesulfonylamino chlorobenzene is dissolved in 100 cc of a twice normal sodium hydroxide solution which has first been brought to 60°C. While maintaining the reaction mixture at this temperature 0.16 mol (27.5 g) of diethylaminoethylchloride hydrochloride in aqueous solution, is added drop by drop, together with 80 cc of a twice normal sodium hydroxide solution which serves to keep the pH sufficiently alkaline. This reaction mixture is kept at 60°C for 30 minutes, cooled, acidified with concentrated hydrochloric acid, and, when then dried, yields 36.5 g of the desired product in the form of its hydrochloride. This crude hydrochloride is purified by crystallization in water, and then converted by addition of a twice normal solution of sodium hydroxide into 2-nitro-4-(N-β-diethylaminoethyl-N-benzenesulfonyl) amino chlorobenzene which, after vacuum drying on $P_2O_5$, melts at 43°C. The analysis of this product yields the following results:

| Analysis | Calculated for $C_{16}H_{22}N_3O_4S\ Cl$ | Found |
|---|---|---|
| C % | 52.49 | 52.25–52.33 |
| H % | 5.35 | 5.17– 5.26 |
| N % | 10.21 | 10.40–10.45 |

Second step: hydrolysis 0.1 mol (4.1 g) of 2-nitro-4-(N-β-diethylaminoethyl-N-benzenesulfonyl)-amino chlorobenzene is heated for two hours in a boiling water bath with 15 cc of concentrated hydrochloric acid. After cooling and adding 30 cc of water, 5 times normal sodium hydroxide is added to bring the pH value to 4, after which drying yields 2.6 g of 2-nitro-4-(N-β-diethylaminoethyl)-amino chlorobenzene monohydrochloride which, after recrystallization in a one tenth normal solution of hydrochloric acid, melts and decomposes at 191°C. Analysis of the product yields the following results:

| Analysis | Calculated for $C_{12}H_{19}N_3O_2Cl_2$ | Found |
|---|---|---|
| C % | 46.75 | 46.88–46.86 |

| Analysis | Calculated for $C_{12}H_{19}N_3O_2Cl_2$ | Found |
|---|---|---|
| H % | 6.16 | 6.33– 6.32 |
| N % | 13.63 | 13.45–13.65 |

In a second series of examples the method of preparing several intermediate compounds responding to formula (IV) will now be described.

EXAMPLE 6

Preparation of (N-methyl-N-acetyl)parachlorometanitraniline 0.19 mol of N-methyl-parachlorometanitraniline, prepared as set forth in example 3, is dissolved in 70 cc of acetic anhydride. This is heated for 15 minutes in a boiling water-bath, and poured into 700 cc of water. Drying then yields 35 g of 2-nitro-4-(N-methyl-N-acetyl)amine chlorobenzene, which melts at 114°C.

EXAMPLE 7

Preparation of 2-nitro-4-(N-methyl N-benzenesulfonyl)-amino chlorobenzene.

0.19 mol (35.5 g) of N-methyl-parachlorometanitraniline prepared as set forth in example 3 is dissolved in 175 cc of pyridine. 0.5 mol (88.25 g) of benzenesulfochloride is added. After heating to reflux for 5 minutes the mixture is cooled, and drying yields 60 g of 2-nitro-4-(N-methyl-N-benzenesulfonyl)-amino chlorobenzene which, after recrystallization in ethyl acetate, melts at 119°C.

EXAMPLE 8

Preparation of 2-nitro-4-(N-benzenesulfonyl-N-β-diethylaminoethyl)-amino chlorobenzene.

0.02 mol (6.16 g) of 2-nitro-4-N-(β-diethylaminoethyl)-amino chlorobenzene is dissolved in 30 cc of pyridine. 0.04 mol, (7.06 g) of benzenesulfochloride is added. After heating to reflux for 20 minutes, this is poured into 100 cc of cold water, and subsequent drying yields 8.9 g of 2-nitro-4-(N-benzenesulfonyl-N-diethylaminoethyl)-amino chlorobenzene monohydrochloride in practically pure form. This hydrochloride, when treated with a twice normal sodium hydroxide solution, yields the corresponding base which, after washing with water and prolonged vacuum drying, melts at 43°C.

EXAMPLE 9

Preparation of 2-nitro-4-(N-acetyl-N-β-acetoxyethyl)-amino chlorobenzene.

0.04 mol (8.6 g) of 2-nitro-4-β-hydroxethylamino chlorobenzene is heated for an hour in a boiling water bath while in solution in 15 cc of acetic anhydride. After driving off the excess acetic anhydride under vacuum, the residue is dissolved by heating it in a mixture containing 40% hexane and 60% benzene. After cooling, drying yields 10.5 g of 2-nitro-4-(N-acetyl-N-β-acetoxyethyl)-amino chlorobenzene which, after recrystallization in the benzene hexane mixture, melts at 60°C. Analysis of this product yields the following results:

| Analysis | Calculated for $C_{12}H_{13}N_2O_5Cl$ | Found |
|---|---|---|
| C % | 47.92 | 48.00–48.04 |
| N % | 9.31 | 9.50– 9.45 |
| H % | 4.32 | 4.45– 4.40 |

In a third series of examples the preparation of certain compounds responding to formula (I) will now be described:

EXAMPLE 10

Preparation of 1-N-β-diethylaminoethylamino-2-nitro-4-(N'-methyl-N'-benzenesulfonyl) amino benzene.

0.2 mol (63.5 g) of 2-nitro-4-(N-methyl-N-benzenesulfonyl) amino chlorobenzene, which has been prepared as described in Example 7, is dissolved in 3.2 mols (371 g) of N,N-diethylethylenediamine. This is heated for four hours at 130°C; and the excess aliphatic diamine driven off under vacuum. The resulting oily residue is dissolved in 500 cc of a normal hydrochloric acid solution, and cooled to 0°C for 24 hours. Drying yields 86 g of 1-N-β-diethylaminoethylamino-2-nitro-4-(N'-methyl-N'-benzenesulfonyl) amino benzene which melts at 145°C. Analysis of the product yields the following results:

| Analysis | Calculated for $C_{19}H_{27}N_4SO_4Cl$ | Found |
|---|---|---|
| N % | 12.65 | 12.90–12.71 |
| S % | 7.22 | 7.38– 7.41 |

The above-described monohydrochloride is treated for two hours with a twice normal sodium hydroxide solution, while stirring vigorously. The sodium hydroxide solution is then extracted with methylisobutyl ketone. The methylisobutylketone, which contains the desired product in solution in the form of its base, is washed with water, dried on sodium sulfate, filtered, and the solvent driven off under vacuum to yield the base in the form of a red oil.

EXAMPLE 11

Preparation of methyl-β-[N-(2-nitro-4-N'-methyl-N'-benzenesulfonyl-amino)phenyl]-aminoethyl methyldiethylammonium sulfate.

In order to carry out this synthesis, the product obtained at the end of example 10 above application is used. 0.148 mol (60 g) of 1-N-β-diethylaminoethylamino-2-nitro-4-(N'-methyl-N'-benzenesulfonyl-)amino benzene is dissolved in 600 cc of cold chlorobenzene and 0.164 mol (16 cc) of methyl sulfate is added drop by drop, while stirring. The reaction mixture is left standing for 24 hours at room temperature. Drying and washing with a little chlorobenzene then yields 74 g of the desired ammonium salt, which melts at 137°C. Analysis of this product yields the following results:

| Analysis | Calculated for $C_{21}H_{32}N_4O_8S_2$ | Found |
|---|---|---|
| N % | 10.53 | 10.77–10.58 |
| S % | 12.03 | 12.12–12.04 |

EXAMPLE 12

Preparation of
1-N-β-hydroxyethylamino-2-nitro-4-(N'-methyl-N'-benzenesulfonyl)amino benzene.

0.153 mol (50 g) of 2-nitro-4-(N-methyl-N-benzenesulfonyl)amino chlorobenzene which has been prepared as described in Example 7 is introduced little by little, while stirring, into 3.06 mols (184 cc) of ethanolamine, which has first been heated to 95°C. The reaction mixture is held for 15 minutes in a boiling water bath and cooled. 2.5 liters of ice water containing 425 cc of concentrated hydrochloric acid are then added. Drying yields 48 g of practically pure 1-N-β-hydroxyethylamino-2-nitro-4-(N'-methyl-N'-benzenesulfonyl)-amino benzene which, after recrystallization in alcohol, melts at 141°C. Analysis of this product yields the following results:

| Analysis | Calculated for $C_{15}H_{17}N_3O_5S$ | Found |
|---|---|---|
| N % | 11.96 | 12.13–11.92 |
| S % | 9.99 | |

EXAMPLE 13

Preparation of
1-N-γ-methoxypropylamino-2-nitro-4-(N'-methyl-N'-benzenesulfonyl)amino benzene.

0.1 mol (32.65 g) of 2-nitro-4-(N-methyl-N-benzenesulfonyl)amino chlorobenzene which has been prepared as indicated in Example 7, is introduced little by little, while stirring, into 2 mols (178 g) of γ-methoxypropylamine which has first been heated to 95°C. The reaction mixture is kept in a boiling water bath for 20 minutes, cooled, and 200 cc of ice water are then poured in. The product is an orange-colored oil, which crystallizes very easily. Drying yields 37 g of practically pure 1-N-γ-methoxypropylamino-2-nitro-4-(N'-methyl-N'benzenesulfonyl)amino benzene, which, after recrystallization in alcohol, melts at 76°C. Analysis of this product yields the following results:

| Analysis | Calculated for $C_{17}H_{21}N_3O_5S$ | Found |
|---|---|---|
| N % | 11.08 | 11.19–11.28 |
| S % | 8.44 | 8.44– 8.55 |

EXAMPLE 14

Preparation of
1-γ-methoxypropylamino-2-nitro-4-(N-methyl-N-acetyl)-amino benzene.

0.1 mol (22.9 g) of N-methyl-parachlorometanitraniline which has been prepared as described in Example 6, is introduced, while stirring, into 1.5 mols (134 g) of γ-methoxypropylamine which has first been heated to 95°C. This reaction mixture is kept at 95°C for 20 minutes, cooled and poured into 1.250 liters of ice water. This is acidified with hydrochloric acid, dried, and washing with water yields 25 g of 1-γ-methoxypropylamino-2-nitro-4-(N-methyl-N-acetyl)amino benzene which, after recrystallization, melts in toluene at 90°C. Analysis of this product yields the following results:

| Analysis | Calculated for $C_{13}H_{19}N_3O_4$ | Found |
|---|---|---|
| C % | 55.52 | 55.77–55.54 |
| H % | 6.76 | 6.85– 6.83 |
| N % | 14.95 | 15.11–15.01 |

EXAMPLE 15

Preparation of
1-N-β-diethylaminoethylamino-2-nitro-4-(N'β-diethylaminoethyl-N'-benzenesulfonyl)amino benzene.

0.05 mol (20.5 g) of 2-nitro-4-(N-β-diethylaminoethyl-N-benzenesulfonyl)-amino chlorobenzene, prepared as described in Example 8, is introduced into 0.5 mol (58 g) of diethylethylenediamine which has first been heated to 95°C. The reaction mixture is kept at this temperature for 30 minutes. The excess aliphatic amine is driven off under vacuum and the oily residue is poured into 200 cc of water. This yields the desired product in the form of a thick oil. The water is decanted; the oil is dissolved in normal hydrochloric acid; the hydrochloric acid solution is filtered and alkalized with a 5 times normal sodium hydroxide solution. The desired product is then extracted, using methylisobutylketone and the solvent driven off under vacuum, yielding 22.6 g of practically pure 1-N-β-diethylaminoethylamino-2-nitro-4-(N'β-diethylaminoethyl-N'-benzenesulfonyl)amino benzene in the form of a very thick oil. Analysis of this product yields the following result:

| Analysis | Calculated for $C_{24}H_{37}N_5O_4S$ | Found |
|---|---|---|
| N % | 14.29 | 14.37–14.46 |
| S % | 6.52 | 6.60– 6.74 |

EXAMPLE 16

Preparation of
1-N-γ-hydroxypropylamino-2-nitro-4-(N-methyl-N-acetyl)-amino benzene.

0.1 mol (22.9 g) of 2-nitro-4-(N-methyl-N-acetyl)-amino chlorobenzene, prepared as described in Example 6 is introduced, while stirring, into 2 mols (150 g) of propanolamine, which has first been heated to 95°C. When this addition has been completed, the mixture is kept at 95°C for 10 minutes, cooled, and poured into 1.5 liters of ice water. It is then acidified with hydrochloric acid, whereupon drying and washing with water yields 25 g of 1-γ-hydroxypropylamino-2-nitro-4-(N-methyl-N-acetyl)-amino benzene which, after recrystallization in toluene, melts at 122°C. Analysis of this product yields the following results:

| Analysis | Calculated for $C_{12}H_{17}N_3O_4$ | found |
|---|---|---|
| C % | 53.93 | 54.14–53.93 |
| H % | 6.37 | 6.37– 6.54 |
| N % | 15.73 | 15.91–15.80 |

EXAMPLE 17

Preparation of
1-N-β-diethylaminoethylamino-2-nitro-4-(N'-β-hydroxyethyl-N'-benzenesulfonyl)-amino benzene.

0.070 mol (25 g) of 2-nitro-4-(N-β-hydroxyethyl-N-benzenesulfonyl)-amino chlorobenzene, which has prepared as described in the foregoing example, is introduced into 0.70 mol (81.5 g) of N,N-diethylethylenediamine which has first been heated to 95°C. The reaction mixture is heated for half an hour in a boiling water bath, and the excess aliphatic amines is then driven off under vacuum. The oily residue obtained in this manner is dissolved in 70 cc of propanol. After having bubbled dry hydrochloric acid through this iced propanolic solution, drying yields 31 g of 1-N-β-diethylaminoethylamino-2-nitro-4-(N'-β-hydroxyethyl-N'-benzenesulfonyl) amino benzene monohydrochloride which, after recrystallization in propanol containing 2% water, melts and decomposes at 178°C. Analysis of this product yields the following results:

| Analysis | Calculated for $C_{20}H_{29}N_4O_5S\ Cl$ | Found |
|---|---|---|
| N % | 11.85 | 11.71–11.82 |
| S % | 6.77 | 6.97– 6.98 |

Several examples will now be given showing how the compounds of formula (1) are used in hair dyeing compositions.

EXAMPLE 18

The following composition is prepared:

| | | |
|---|---|---|
| 1-N-β-diethylaminoethylamino-2-nitro-4N'-hydroxyethylamino benzene dihydrochloride | 0.37 | g |
| 1-N-γ-hydroxypropylamino-2-nitro-4-(N-methyl-N-acetyl)-amino benzene | 0.26 | g |
| Isooctylphenylpolyethoxyethanol | 1.2 | g |
| $Na_2CO_3$, q.s.p. | pH | 8 |
| Water, q.s.p. | 100 | g |

This composition is applied to bleached hair and left thereon for 10 minutes. The hair is then rinsed and shampooed.

A copper mahogany color results.

EXAMPLE 19

The following composition is prepared:

| | | |
|---|---|---|
| 1-N-γ-hydroxypropylamino-2-nitro-4-(N-methyl-N-acetyl)-amino benzene | 1.3 | g |
| Isooctylphenylpolyethoxyethanol | 1.5 | g |
| $NH_4OH$, q.s.p. | pH | 9 |
| Water, q.s.p. | 100 | g |

This composition is applied to 100% white hair for 15 minutes. The hair is then rinsed and shampooed and a deep blonde shade results.

EXAMPLE 20

The following dyeing composition is prepared:

| | |
|---|---|
| 1-diethylaminoethylamino-2-nitro-4-N,N-dihydroxyethylamino benzene dihydrochloride | 0.30 g |
| Methyl-β-[N(2-nitro-4-N'-methyl-N'-benzenesulfonylamino)-phenyl]-aminoethyl-methyldiethylammonium sulfate | 0.14 g |
| Isooctyl phenyl polyethoxy ethanol | 1.2 g |
| Monoethanolamine, q.s.p. | pH 7.5 |
| Water, q.s.p. | 100 g |

This composition is applied to bleached hair and left thereon for 10 minutes. The hair is then rinsed and shampooed.

A deep mahogany blond results.

EXAMPLE 21

The following dyeing composition is prepared:

| | |
|---|---|
| 1-N-βdiethylaminoethyl amino-2-nitro-4-N'-hydroxy-ethylamino benzene | 0.25 g |
| Isooctyl phenyl polyethoxyethanol | 1.2 g |
| Lactic acid q.s.p. | pH 4 |
| Water q.s.p. | 100 g |

This composition is applied to bleached hair and left thereon for 10 minutes. The hair is then rinsed and shampooed.

A purple-violet color results.

The dyes of the invention can be also applied to normal colored hair and without using an oxidizing agent.

The following dye compounds illustrate the compounds of the invention containing respectively the R, Z, R', R'', $R_1$, $R_2$ and $R_3$ radicals as before mentioned: 1-N-β-hydroxyethylamino-2-nitro-4-(N'-methyl-N'-benzenesulfonyl)amino benzene; 1N-β-diethylaminoethylamino-2-nitro-4-(N'-β-hydroxyethyl-N'-benzenesulfonyl)-amino benzene; 2-nitro-4-(N-acetyl-N-β-acetoxyethyl)-amino chlorobenzene; 1-methylamino-2-nitro-4-(N,N-methyl, carboxymethyl) amino benzene; 1-N-methylamino-2-nitro-4-(N'-benzenesulfonyl, N'-β-bromoethyl)amino benzene; 2-nitro-4-N-(βN-(β-diethylaminoethyl)-amino chlorobenzene; 1-N-β-diethylaminoethylamino-2-nitro-4(N'-β-diethylaminoethyl-N'-benzenesulfonyl)amino benzene; 1-N-γ-methoxypropylamino-2-nitro-4-(N'-methyl-N'-benzenesulfonyl)amino benzene; 1-N-β-diethylaminoethylamino-2-nitro-4-(N'-methyl-N'-benzenesulfonyl) amino benzene.

The following organic solvents may be used as solvent in the dye composition of this invention: benzylic alcohol, phenethyl alcohol, 2-butoxyethanol, cyclohexanol and the like.

The ingredients which may be added to the dye composition of this invention of the conventional type and particularly of the dyes selected from the group consisting of nitro dyes such as 1-hydroxy-2-amino-5-nitro benzene, azo dyes known commercially as "Supracide", "Supramine", "Cibacete" and "Solacete", and anthraquinone dyes known commercially as "Solway", "Cellit" and "Fenacet".

The following compounds illustrate the intermediate compounds of the invention:

1-chloro-2-nitro-4-(N-methyl-N-acetyl)-amino benzene;

1-chloro-2-nitro-4-(N-methyl-N-benzenesulfonyl)-amino benzene;

1-chloro-2-nitro-4-(N'-diethylaminoethyl -N'benzenesulfonyl)amino benzene;

1 chloro-2-nitro-4-(N-carbomethoxy-ethyl-N-acetyl-)amino benzene;

1-chloro-2-nitro-4-(N-carbethoxy-ethyl-N-benzenesulfonyl)amino benzene;

1-chloro-2-nitro-4-(N-bromoethyl-N-benzenesulfonyl)amino benzene, which have the respective formulas:

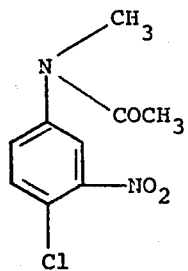 , 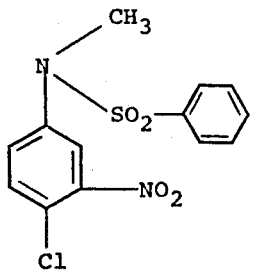 ,

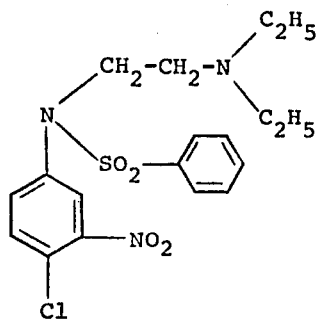 , 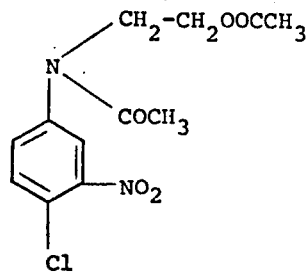 ,

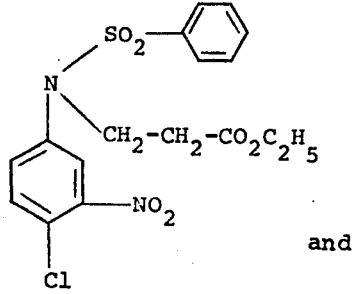 and 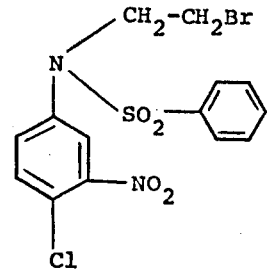

What is claimed is:
1. A compound of the formula

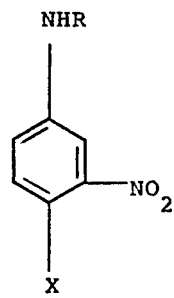

wherein R is selected from the group consisting of -alkylaminodialkyl, -alkylmorpholino and -alkylpiperidino and X represents halogen, the alkyl portion of R having 1 to 6 carbon atoms, and the salts of said compound.

2. The compound of claim 1 selected from the group consisting of 2-nitro-4-N-(β-diethylaminoethyl)-amino chlorobenzene and the monohydrochloride thereof.

* * * * *